US010322280B2

(12) United States Patent
Buczynski et al.

(10) Patent No.: US 10,322,280 B2
(45) Date of Patent: Jun. 18, 2019

(54) MICROPROBE FOR SELECTIVE ELECTROPORATION AND MANUFACTURING METHOD OF SUCH A MICROPROBE

(71) Applicant: INSTYTUT TECHNOLOGII MATERIALOW ELEKTRONICZNYCH, Warsaw (PL)

(72) Inventors: Ryszard Buczynski, Warsaw (PL); Dariusz Pysz, Warsaw (PL); Ryszard Stepien, Warsaw (PL)

(73) Assignee: INSTYTUT TECHNOLOGII MATERIALOW ELEKTRONICZNYCH, Warsaw (PL)

( * ) Notice: Subject to any disclaimer, the term of this patent is extended or adjusted under 35 U.S.C. 154(b) by 45 days.

(21) Appl. No.: 15/519,444

(22) PCT Filed: Oct. 21, 2015

(86) PCT No.: PCT/EP2015/074354
§ 371 (c)(1),
(2) Date: Apr. 14, 2017

(87) PCT Pub. No.: WO2016/062761
PCT Pub. Date: Apr. 28, 2016

(65) Prior Publication Data
US 2017/0239469 A1     Aug. 24, 2017

(30) Foreign Application Priority Data
Oct. 21, 2014  (PL) .......................................... 409831

(51) Int. Cl.
*A61N 1/04*     (2006.01)
*A61N 1/32*     (2006.01)
(Continued)

(52) U.S. Cl.
CPC ........... *A61N 1/327* (2013.01); *A61N 1/0412* (2013.01); *C12M 35/02* (2013.01); *A61B 18/14* (2013.01);
(Continued)

(58) Field of Classification Search
None
See application file for complete search history.

(56) References Cited

U.S. PATENT DOCUMENTS 3,282,817 A  *  11/1966  Riseman ................ G01N 27/36
                                                      204/409
4,312,734 A  *   1/1982  Nichols .................. G01N 27/36
                                                      204/420
(Continued)

FOREIGN PATENT DOCUMENTS

| EP | 2497419 A1 | 9/2012 |
|---|---|---|
| JP | 2004041434 A | 2/2004 |
| WO | 03/046170 A1 | 6/2003 |

OTHER PUBLICATIONS

International Search Report dated Mar. 11, 2016 corresponding to International Application No. PCT/EP2015/074354, citing the above reference(s).
(Continued)

*Primary Examiner* — Kennedy Schaetzle
(74) *Attorney, Agent, or Firm* — Hauptman Ham, LLP

(57) ABSTRACT

The subject of the invention is a microprobe for selective electroporation comprising at least two metal electrodes (A) immersed in a glass rod (E), characterized in that the glass rod (E) made of a primary glass is 50 μm to 2 mm in diameter, preferably 50 μm to 500 μm, the metal electrodes (A) made of a metal alloy are formed as rods with diameter of 1 μm to 100 μm, preferably 20 μm to 30 μm, wherein endings of those rods are exposed,
(Continued)

wherein the primary glass and the metal alloy are matched in such manner that dilatometric softening temperature DTM of the primary glass is highly similar to the temperature of melting for the metal alloy.

The invention also includes a method of manufacturing of such a microprobe.

8 Claims, 4 Drawing Sheets

(51) Int. Cl.
  *C12M 1/42* (2006.01)
  *A61B 18/14* (2006.01)
  *A61B 18/00* (2006.01)

(52) U.S. Cl.
  CPC ..... *A61B 2018/00613* (2013.01); *A61N 1/048* (2013.01)

(56) References Cited

U.S. PATENT DOCUMENTS

| | | | |
|---|---|---|---|
| 4,969,468 A * | 11/1990 | Byers | A61B 5/0422 29/829 |
| 5,388,577 A * | 2/1995 | Hubbard | G01N 33/4836 257/448 |
| 6,304,784 B1 | 10/2001 | Allee et al. | |
| 2001/0020167 A1* | 9/2001 | Woloszko | A61B 18/1402 606/45 |
| 2002/0198446 A1 | 12/2002 | Hill et al. | |
| 2007/0088208 A1* | 4/2007 | Yasuzawa | A61B 5/04001 600/345 |
| 2011/0295347 A1* | 12/2011 | Wells | A61N 5/0601 607/89 |
| 2013/0001090 A1* | 1/2013 | Rubinson | A61N 1/04 205/118 |
| 2013/0030274 A1 | 1/2013 | Jamieson et al. | |
| 2013/0046148 A1* | 2/2013 | Tathireddy | A61B 5/04001 600/300 |
| 2014/0222123 A1 | 8/2014 | Cui et al. | |
| 2015/0151107 A1* | 6/2015 | Schouenborg | A61N 1/05 600/377 |
| 2017/0087352 A1* | 3/2017 | Ek | A61N 1/05 |
| 2017/0303381 A1* | 10/2017 | Wang | H05H 1/26 |

OTHER PUBLICATIONS

C. Chen et al., "Membrane electroporation theories: a review", International Federation for Medical and Biological Engineering 2006, Feb. 2, 2006, vol. 44, p. 5-14.

Jochen De Vry et al., "In vivo electroporation of the central nervous system: A non-viral approach for targeted gene delivery", Progress in Neurobiology, Oct. 1, 2010, vol. 92, p. 227-244.

* cited by examiner

Fig. 1
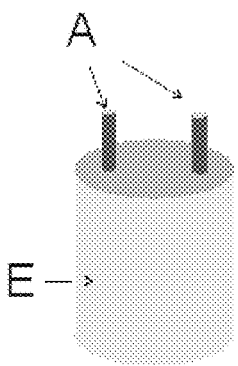
Fig. 2
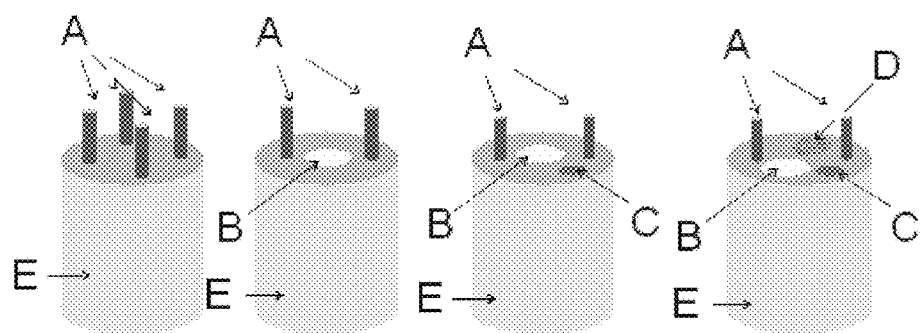
Fig. 3
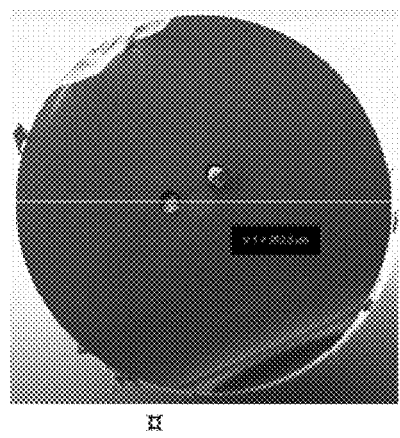 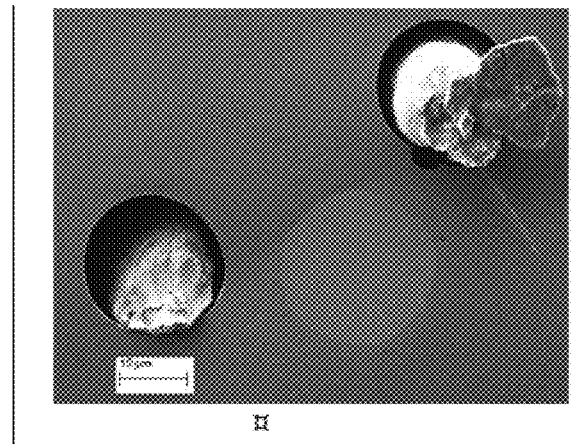

Fig. 4
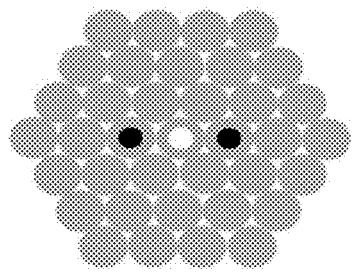
Fig. 5a            Fig. 5b
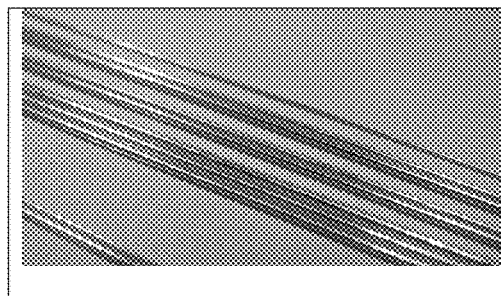 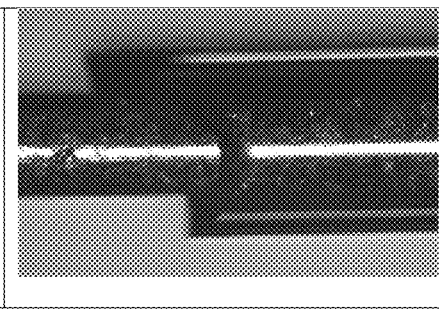
Fig. 6
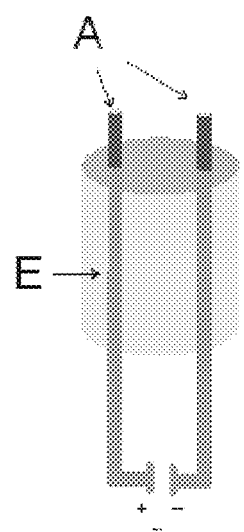

Fig. 7
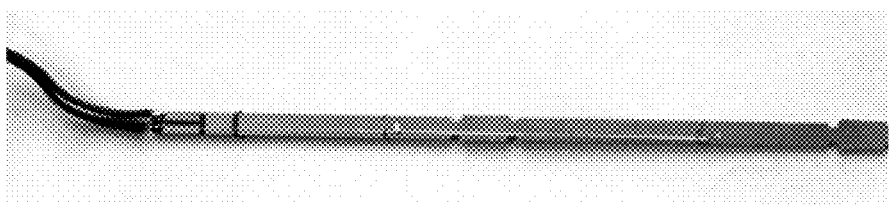
Fig. 8a
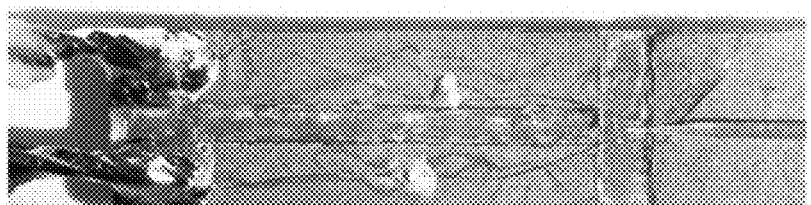
Fig. 8b
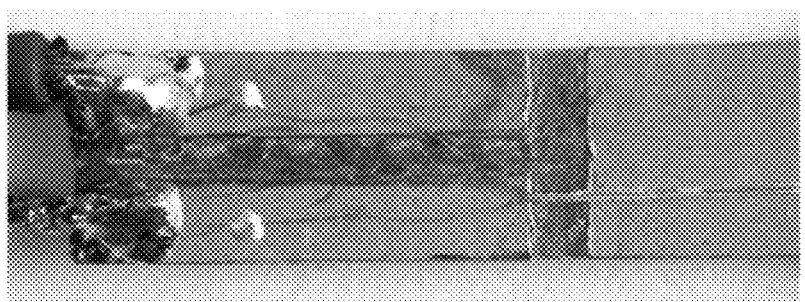
| Fig. 9a | Fig. 9b | Fig. 9c |
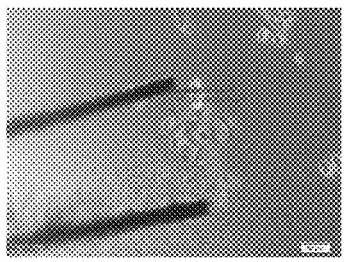 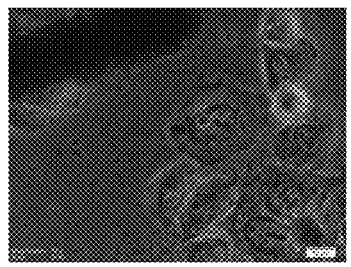 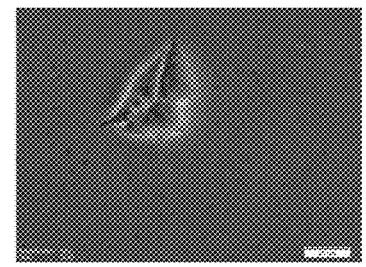

Fig. 10a
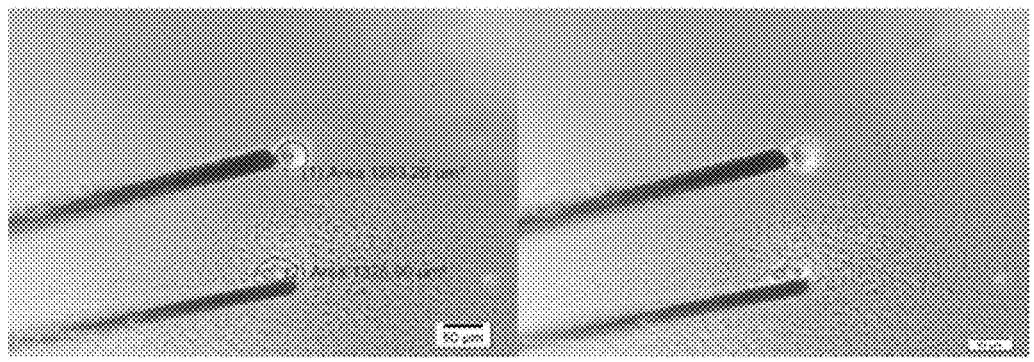
Fig. 10b
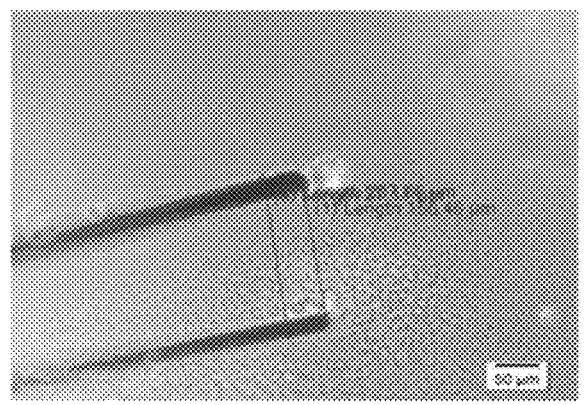
Fig. 10c Fig. 10d
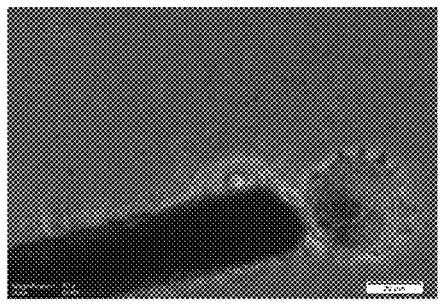 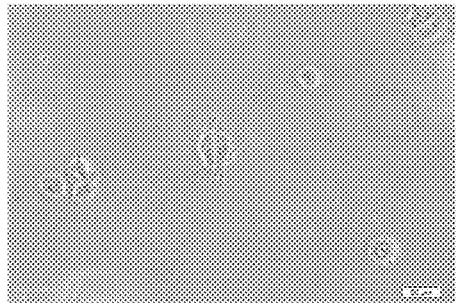

though reciprocal dependence between metal alloy melting temperature and dilatometric softening temperature DTM for the primary glass, what leads to capillary thinning, is possible.

MICROPROBE FOR SELECTIVE ELECTROPORATION AND MANUFACTURING METHOD OF SUCH A MICROPROBE

CROSS REFERENCE TO RELATED APPLICATION

This present application is a national stage filing under 35 U.S.C. § 371 of PCT application number PCT/EP2015/074354 filed on Oct. 21, 2015 which is based upon and claims the benefit of priority to Polish Patent Application No. PL409831 filed on Oct. 21, 2014 in the Polish Intellectual Property Office. The disclosures of the above-listed applications are hereby incorporated by reference herein in their entirety.

BACKGROUND

Electroporation is one of the delivery methods used experimentally to open cell membranes in living organisms and to deliver internally biologically active compounds or to isolate fragments of cells from their interior, e.g. DNA. Method is based on generation of local electromagnetic field what leads to disruption of cell membrane electron structure and generation of channels where molecules can migrate intracellularly [De Vry, Jochen (2010) *In vivo electroporation of the central nervous system: A non-viral approach for targeted gene delivery*. Progress in Neurobiology 92(3)]. Electroporation is used as a experimental method for gene therapy and for treatment of i.a. neoplastic diseases where electric field enables local disintegration of cell membrane and precise delivery of new generation drugs to the malignant cells. The benefit of electroporation is a possibility of local delivery of highly toxic anticancer drugs without a need to apply general chemotherapy which is destructive for a whole organism [C. Chen, S. W. Smye, M. P. Robinson i J. A. Evans, *Membrane electroporation theories: a review*, Medical and Biological Engineering and Computing, tom 44, 1-2 (2006), 5-14].

In the art there are macroscopic probes known in form of needles or macroscopic plates which are utilized for surface treatment, especially skin cancer (e.g. melanoma), or for electroporation of whole cell cultures without in vitro selectivity. Existing solutions do not support electroporation of single cell in in vitro culture, nor electroporation of internal organs in very limited region. Method for probes manufacturing used so far utilizes lithographic methods based on repetitive fibre etching and application of metal and dielectric layers. In those methods material with different structures are mixed by spraying and process of pulling, so called probe shaft thinning, is utilized. Probes manufactured according to preceding method are not thin enough (minimally about 1 mm) in order to act selectively and have limited length. Additionally, quality of obtained gaps and light-conductive cores in such probes is low. Probes obtained using lithographic method exhibit low thermal resistance and low bending and stress resistance and their functionality reflected in e.g. drug delivery (through channels in shafts of such probes) is extremely limited.

From U.S. Pat. No. 6,304,784 (B1) publication there is known a flexible probe manufactured using preceding methods with about 1 mm in diameter with cylindrical cross-section designed for electric stimulation of internal organs. Probe contain electric wires transferring electric signals to different fragments of probe on whole length of its shaft.

Similarly, EP2497419 (A1) publication discloses method for manufacturing of flexible probe with cylindrical cross-section involving lithographic methods for brain cells stimulation. Probe according to this publication contains electrodes on its surface which are covered with thin layer of isolating material with 0.5 mm thickness.

From US2002/0198446 (A1) publication there is known a probe with cylindrical rigid core containing many electrodes extending over its surface and method of manufacturing of a probe comprising lithographic methods and comprising covering stage with thin layer of isolating material.

On the other hand neuroprobe from US2013/0030274 (A1) publication consists of one or more shafts and contains optical source connected with at least one optical fibre stretched on whole length of probe shaft or shafts. Also in this invention lithographic method for probe manufacturing has been utilized what is connected with manufacturing of electrodes on the surface of semiconductive material containing waveguides and metal lines prepared using lithography.

DETAILED DESCRIPTION

Preceding solutions do not enable utilizing of electroporation phenomenon to selectively open cell membrane i.e. in case of single cells or in limited regions, for example for electroporation of internal organs. In this way there is a need to develop such a probe, which thanks to smaller dimensions than before, would reach single cells or limited regions in patient body and which would be used as a tool for selective electroporation.

Subject of the invention is a microprobe for selective electroporation of chosen cells regions of internal organs in vivo and single cells in vitro and also for additional integration in one device: channel for local drug delivery, imaging channel for observation of region where electroporation is applied, optical fibre for delivery or receiving of illuminating or therapeutic signal. Subject of the invention is also method of manufacturing of such a microprobe.

The subject of the present invention is a microprobe for selective electroporation containing at least two metal electrodes immersed in a glass rod characterised in that the glass rod, which is made of a primary glass, has the diameter 50 µm to 2 mm, preferably 50 µm to 500 µm, the metal electrodes made of a metal alloy are made in form of rods with 1 µm to 100 µm in diameter, preferably 20 µm to 30 µm, where endings of those rods are exposed, wherein the primary glass and the metal alloy are matched in this way that dilatometric softening temperature for primary glass is close to the melting temperature of metal alloy. Construction of microprobe metal electrodes enables constant transduction of electricity or voltage potential is generated, and are isolated from each other and from surroundings by glass. The whole set is small, integrated, long and in form of a fibre.

Preferably the metal alloy exhibits melting temperature lower than dilatometric softening temperature DTM for the primary glass, preferably not more than 50° C. lower, wherein preferably dilatometric softening temperature for the primary glass equals at most 610° C. Such a match of temperatures enables pulling of capillary structure with metal inside—metal temperature must be lower than temperature of glass, what is a condition for carrying out the process of thinning in the tower. Lower metal alloy melting temperature difference and dilatometric softening temperature DTM for the primary glass is better because metal is less stretched and thanks to that it obtains a proper structure.

Because of that metal alloy and glass composition should be matched in that manner that the difference is possibly lowest and not higher than 50° C. Simultaneously, low dilatometric softening temperature DTM for the primary glass enables better formation of microprobe structure.

In preferable embodiment of the invention metal alloy is silver alloy, preferably silver and tin, for example it is a BAg7(Ag56Sn) alloy. In selection of silver alloys low dilatometric softening temperature DTM of the primary glass is preferable. BAg7(Ag56Sn) is an alloy with good transmission parameters fitted to dilatometric softening temperature DTM of the primary glass.

Preferably, microprobe according to the invention is equipped in at least one air channel for drug delivery, preferably with 2 µm to 1500 µm in diameter, located inside the glass rod.

Preferably, microprobe according to the present invention is equipped in at least one optical channel, preferably made of secondary glass, for transmission of optical signal, preferably with 1 µm to 300 µm in diameter, located inside the glass rod.

In other preferred embodiment, microprobe according to the present invention comprises at least one imaging channel made of a secondary glass for transmission of optical image, preferably 50 µm to 1500 µm in diameter, located inside glass rod.

Preferably refractive index $n_D$ of the primary glass is lower than refractive index $n_D$ of the secondary glass, preferably of least 0.001 lower, and more preferably at least 0.01 lower, and most preferably at least 0.5 lower, for example refractive index $n_D$ of primary glass equals 1.51 and refractive index $n_D$ of the secondary glass equals at most 2.49. The higher index difference, the smaller imaging channels and more channels can be inserted in given structure and obtain higher imaging resolution. It is highly important because these kind of glass, so called "thermally fitted", can be thinned on fibre optic tower (i.e. generate preferable structure in elevated temperature conditions), and after cooling down such a structure will be stable and will not exhibit internal stresses which can lead to spontaneous structure disintegration, and will be resistant to bending.

Preferably linear thermal expansion coefficient of the primary glass and the secondary glass are similar, wherein preferably for the primary glass in 20-300° C. temperature range linear thermal expansion coefficient is equal to 84.0 $10^{-7}K^{-1}$, and in 20-450° C. temperature range is equal to 89.0 $10^{-7}K^{-1}$ or preferably, linear expansion coefficient for the secondary glass in 20-300° C. temperature range is equal to 89.7 $10^{-7}K^{-1}$, and in 20-450° C. temperature range is equal to 94.5 $10^{-7}K^{-1}$. It is always preferable that difference between thermal expansion coefficients for the primary glass and the secondary glass was as low as possible. It is important that glass can be treated thermally together (structure thinning in elevated temperature) and subsequently cooled down avoiding generation of high internal structure stresses which could lead to spontaneous disintegration of the structure or under the influence of bending, touch, etc.

Preferably, the primary glass can be chosen from the group consisting of SK222, NC-21A, PBG-89, F2 Schott, KB-03 glass or the secondary glass is selected from the group consisting of Zr3/XV, NC-32, NC-41, LLF1 Schott, F2 Schott, PBG-08 (PBG81), F2/1,67/2, PBS-57A glass. These are sorts of glass which enable thermal transformation in process of microprobe manufacturing and are not crystallizing during such a transformation. It is important that each glass from this group is paired thermally with appropriate primary glass.

The invention also covers a method for manufacturing of microprobe for selective electroporation, especially microprobe according to the preceding claims 1-9, wherein method of thinning is utilized, characterised in that, it covers following steps:
a) inserting of the rod made of a primary glass with core made of metal alloy in a capillary made of the primary glass, wherein the capillary preferably is generated previously by pulling,
b) subjecting of the product from step a) to thinning process in anaerobic atmosphere inside the capillary,
c) preparation of a preform comprising:
product of step b) in amount of at least 2 units,
and rods made of the primary glass,
placed together in the tube made of the primary glass, wherein preferably preform from step c) contains additionally at least one optical fibre rod made of a secondary glass,
d) treatment of the preform of step c) using thinning process on a fibre optic tower with pressure control assurance and in protective atmosphere (e.g. anaerobic) inside the preform with generation
of a glass rod (E) made of the primary glass with 50 µm to 2 mm in diameter, preferably 50 µm to 500 µm and,
metal electrodes (A) made of a metal alloy formed as a rods with 1 µm to 100 µm in diameter, more preferable 20 µm to 30 µm,
wherein the primary glass and the metal alloy are matched in such manner that dilatometric softening temperature DTM of the primary glass is highly similar to the temperature of melting for the metal alloy.

Capillaries from the primary glass enable generation of a channel along the microprobe for drug delivery or to obtain samples from the region or into the region where electrostatic field is generated or where current flows—i.e. on the end of the microprobe with electrodes exposed. Exposing of the microprobe ends is relevant, because thanks to that it is possible to control region where electric field is generated, optionally region where the current flows (current will flow only through the region where exposed microprobe ends are located i.e. electrode endings). Moreover, in the process of manufacturing of microprobe construction, capillaries made of the primary glass enable insertion of metal rod into the construction which in this process will be enclosed in the capillary after integration with thinning. Optical fibre rod made of secondary glass after integration with other preform elements after thinning will become so called optical fibre core—which enables therapeutic signal delivery to the electroporated region or picking up the optical signal from the electroporated region for analysis.

Many optical fibre rods made of secondary glass after integration with other preform elements can constitute imaging channel after thinning, wherein each rod will transfer one image element (pixel).

Preferably, after step d) there occurs a process of electrode uncovering on the end of the microprobe, especially using etching method, and subsequently electrodes of the probe are connected to the external power supply by mounting the probe to an underlay plate.

Preferably, the etching method with a solution of hydrofluoric acid is utilized, wherein preferably when acid to water ratio in solution of hydrofluoric acid equals 1:1, and more preferably, when etching time equals 30 minutes.

Preferably, the metal alloy with melting temperature lower than dilatometric softening temperature DTM of the primary glass is utilized, preferably no more than 50° C. lower, wherein preferably the metal alloy is silver alloy, preferably silver and tin alloy, for example BAg7 (Ag56Sn) alloy, and dilatometric softening temperature DTM for the primary glass equals 610° C. at most.

Preferably, linear thermal expansion coefficients of the primary glass and the secondary glass are similar, wherein preferably for the primary glass in 20-300° C. temperature range linear thermal expansion coefficient is equal to 84.0 $10^{-7}K^{-1}$, and in 20-450° C. temperature range is equal to 89.0 $10^{-7}K^{-1}$ or preferably, linear expansion coefficient for the secondary glass in 20-300° C. temperature range is equal to 89.7 $10^{-7}K^{-1}$, and in 20-450° C. temperature range is equal to 94.5 $10^{-7}K^{-1}$. It is always preferable that difference between thermal expansion coefficients for the primary glass and the secondary glass is as low as possible. It is important that glass simultaneously can be treated thermally together (structure thinning in elevated temperature) and subsequently cooled down avoiding generation of high internal structure stresses, which could lead to spontaneous disintegration of the structure or under the influence of bending, touch, etc.

In preferred embodiment, refractive index $n_D$ of the primary glass is lower than refractive index $n_D$ of the secondary glass, preferably of least 0.001 lower, and more preferably at least 0.01 lower, more preferably at least 0.5 lower, for example refractive index $n_D$ of the primary glass equals 1.51 and refractive index $n_D$ of the secondary glass equals at most 2.49. The higher index difference, the smaller imaging channels and more channels can be inserted in given structure and obtain higher imaging resolution. It is highly important because these kind of glass, so called "thermally fitted", can be thinned on fibre optic tower (i.e. generate preferable structure in elevated temperature conditions), and after cooling down such a structure will be stable and will not exhibit internal stresses which can lead to spontaneous structure disintegration, and will be resistant to bending.

Preferably, the primary glass can be chosen from the group consisting of SK222, NC-21A, PBG-89, F2 Schott, KB-03 glass or the secondary glass selected from the group consisting of Zr3/XV, NC-32, NC-41, LLF1 Schott, F2 Schott, PBG-08 (PBG81), F2/1,67/2, PBS-57A glass. These are sorts of glass which enable thermal transformation in process of microprobe manufacturing and are not crystallizing during such a transformation. It is important that each glass from this group is paired thermally with appropriate primary glass.

Microprobe according to the invention exhibits monolithic structure in form of fibre and can be utilized for in vivo applications using biopsy needle or for in vitro applications. Microprobe parameters according to the present invention i.e. flexibility, resistance to temperature and stresses, are obtained thanks to selection of materials with good rheological characteristics, fitted thermally, integrated in thinning process on fibre optic tower, in order to obtain stable, integrated microprobe structure without internal stresses.

Due to the small distance between electrodes, in order to generate electric field needed for electroporation of cells, voltage of only few V needs to be applied instead of voltage in kilovolt range needed for standard macroscopic electroporation devices. Thanks to that microprobe according to the present invention can be charged using batteries.

Method for microprobe manufacturing according to the invention enables mass production of microprobes with identical geometric parameters. Used pulling process, so called drawing down at the fibre optic drawing tower, enables manufacturing of microprobes with length of many meters with identical transverse parameters, which can be further cut on many microprobes of given length.

PREFERRED EMBODIMENTS OF THE INVENTION

Invention will be explained closer in the preferred embodiments, with references to the given figures, where:

FIG. 1 presents microprobe scheme according to the invention, with two metal electrodes A integrated into flexible glass fibre, so called glass rod E, FIG. 2 presents microprobe scheme according to the invention with additional functions integrated with microprobe shown on the FIG. 1.

FIG. 3 presents SEM images of microprobe cross-sections according to the invention with two metal electrodes A, FIG. 4 presents preform cross-section for microprobe thinning according to the invention with two metal electrodes A, FIG. 5a-b presents view on the glass rods E with metal core obtained by pulling (drawing down), FIG. 6 presents scheme of charging for microprobe according to the present invention, FIG. 7 presents microprobe according to the invention with a grip enabling connection to the electricity and mechanical adjustment to the sample, FIG. 8a-b presents connection by connecting with conductive gluing of E glass rods of microprobe E according to the invention with macroscopic electric wires, FIG. 9a-c presents results from CHO-K1—(ATCC® CCL-61™) cells electroporation measurements described in example 3, and FIG. 10a-d presents results from H9C2 cells electroporation measurements—cells of rat cardiac muscle described in example 3.

On the figures following descriptions has been used: A—metal electrode, B—air channel, C—optical channel, D—imaging channel, E—glass rod.

Following materials have been used for manufacturing of microprobes:

Microprobe design: tubes and rods made of primary glass, i.e. SK222 glass (thermometric type glass made by Krosno Glassworks)

Optical channel C: secondary glass rods, i.e. Zr3/XV glass (designed and melted in ITME)

Metal electrodes A: rods 2 mm in diameter made of BAg7 (Ag56Sn) alloy (manufacturer—Lucas-Milhaupt Gliwice)

Characteristics of the materials are enlisted in Table 1 and 2:

TABLE 1

| Characteristics of Bag7 alloy used for construction of GM1A microprobes. ||
| --- | --- |
| Characteristic | BAg7 alloy |
| Composition [%] | Ag 56 |
|  | Cu: 22 |
|  | Zn: 17 |
|  | Sn: 5 |
| Melting temp. [° C.]: | 620-650 |
| Density [g/cm$^3$] | 9.4 |
| Stretching resistance [kg/mm$^2$] | 48 |

TABLE 2

Characteristics of glass used for construction of GM1A microprobes.

| Characteristic | Primary glass SK222 | Secondary glass Zr3/XV |
|---|---|---|
| Refractive index $n_D$ | 1.520 | 1.609 |
| Linear thermal expansion coefficient for range of: | | |
| 20-300° C. $[10^{-7}K^{-1}]$ | 84.0 | 89.7 |
| 20-450° C. $[10^{-7}K^{-1}]$ | 89.0 | 94.5 |
| Transformation temperature Tg [° C.] | 542 | 581 |
| Dilatometric softening temperature DTM [° C.] | 610 | 644 |
| Temperatures distinctive for Leitz heating microscope: | | |
| Temperature of [° C.] | | |
| curvature | 700 | 680 |
| generation a spherical shape | 820 | 790 |
| generation a semispherical shape | 950 | 865 |

Linear thermal expansion coefficients for the primary glass and the secondary glass are similar. SK222 glass and Bag7 alloy are chosen due to the alloy melting temperature which is about 50° C. lower than temperature of thinning for the glass. That provides metal liquidity during glass capillary stretching and limits generation of gaps in elongated glass-metal rods. Relatively high thermal expansion coefficient for the primary glass—SK222 glass ($89 \times 10^{-7}K^{-1}$ for 20-450° C. range) lead to the reduction of tensions on glass-metal interface. Zr3/XV secondary glass is matched with primary SK222 glass in terms of refractive index and thermal expansion coefficient making imaging channel D for transmission of optical image with good mechanical properties.

For realisation of present invention it is possible to choose different glass types which are thermally compatible in rheological terms. Below thermally compatible glass pairs with their qualitative-quantitative composition and refractive index n D are presented:

| NC-21A and NC-32: | | | |
|---|---|---|---|
| NC-21A Composition | Concentration [% mol] | NC-32 Composition | Concentration [% mol] |
| SiO$_2$ | 56.84 | SiO$_2$ | 54 |
| B$_2$O$_3$ | 23.19 | B$_2$O$_3$ | 21 |
| Al$_2$O$_3$ | 0.61 | Al$_2$O$_3$ | 0.5 |
| Li$_2$O | 6.23 | Li$_2$O | 5 |
| Na$_2$O | 9.51 | Na$_2$O | 8.5 |
| K$_2$O | 3.63 | K$_2$O | 3 |
| | | BaO | 5 |
| $n_D = 1.5273$ | | $n_D = 1.5538$ | |

| NC-21A and NC-41: | | | |
|---|---|---|---|
| NC-21A Composition | Concentration [% mol] | NC-41 Composition | Concentration [% mol] |
| SiO$_2$ | 56.84 | SiO$_2$ | 54.5 |
| B$_2$O$_3$ | 23.19 | B$_2$O$_3$ | 22 |
| Al$_2$O$_3$ | 0.61 | Al$_2$O$_3$ | 1.5 |
| Li$_2$O | 6.23 | Li$_2$O | 5 |
| Na$_2$O | 9.51 | Na$_2$O | 8 |
| K$_2$O | 3.63 | K$_2$O | 5 |
| | | PbO | 3 |
| | | BaO | 1 |
| $n_D = 1.5273$ | | $n_D = 1.5374$ | |

| NC-21A and LLF1 Schott: | |
|---|---|
| $n_D = 1.5273$ | $n_D = 1.5481$ |

| NC-21A and F2 Schott: | |
|---|---|
| $n_D = 1.5273$ | $n_D = 1.6200$ |

| PBG-89 and PBG-08: | | | |
|---|---|---|---|
| PBG-89 Composition | Concentration [% mol] | PBG-08 (PBG81) Composition | Concentration [% mol] |
| SiO$_2$ | 45 | SiO$_2$ | 40 |
| Ga$_2$O$_3$ | 10 | Ga$_2$O$_3$ | 13 |
| Bi$_2$O$_3$ | 10 | Bi$_2$O$_3$ | 10 |
| PbO | 28 | PbO | 30 |
| CdO | 3 | CdO | 7 |
| ZnO | 4 | | |
| $n_D = 1.9060$ | | $n_D = 1.9379$ | |

| F2 Schott and F2/1.67/2 | | |
|---|---|---|
| F2 Schott | F2/1.67/2 Composition | Concentration [% mol] |
| | SiO$_2$ | 60.7 |
| | Al$_2$O$_3$ | 3 |
| | PbO | 28 |
| | K$_2$O | 4 |
| | Na$_2$O | 4 |
| | As$_2$O$_3$ | 0.3 |
| $n_D = 1.6200$ | $n_D = 1.6543$ | |

| KB-03 and PBS-57A | | | |
|---|---|---|---|
| KB-03 Composition | Concentration [% mol] | PBS-57A Composition | Concentration [% mol] |
| B$_2$O$_3$ | 62.97 | SiO2 | 53.10 |
| ZnO | 6.57 | PbO | 44.20 |
| CaO | 9.53 | Al$_2$O$_3$ | 0.65 |
| Na$_2$O | 16.16 | Na$_2$O | 0.86 |
| NaF | 4.77 | K$_2$O | 0.85 |
| | | As$_2$O$_3$ | 0.33 |
| $n_D = 1.5415$ | | $n_D = 1.8467$ | |

Example 1—Microprobe for Electroporation

In present embodiment microprobe for electroporation presented on scheme FIG. 1 and on the SEM image on FIG. 3, is a glass rod E with two integrated metal electrodes A. Alternatively, microprobe contains higher amount of metal electrodes A, what is depicted on FIG. 2, being in form of microwires, and immersed in glass rod E. Continuous and long metal electrodes A exhibit small diameters equal to 29 μm and 28 μm, respectively, and distance between them equals to 37 μm. External diameter of glass rod equals to 458 μm.

Depending on the additional application microprobes are integrated in one unit also with other elements such as imaging channel D for transmission of optical image, optical channel C for transmission of optical signal or air channel B for drug delivery.

Example 2—Manufacturing of GM1A Type Microprobe Containing Optical Channel C for Transmission of Optical Image Process for microprobe manufacturing is performed in few steps:
  Manufacturing of capillaries from SK222 glass with 2 mm internal diameter and internal/external diameter ratio equal to about 0.5. For this purpose from ϕext/ϕint 15/11 tubes ϕext 10 were pulled out and after combination with ϕext 15 final capillaries were pulled out with 4.2/2 ϕext/ϕint dimensions.

Pulling of E glass rods with metal core.

Rod made of BAg7 alloy after polishing and defatting was placed in immersed capillary made of SK222 glass. Capillary was pumped out and flushed with argon few times before thinning in order to remove oxygen and to avoid metal oxidation. During thinning process anaerobic conditions were sustained inside the capillary (argon). Rods were drawn down (with metal core) with 0.3-1.1 external diameter, presented on FIG. 2.

Pulling of C glass rods for transmission of optical image.

Optical fibre structure rods were manufactured using "rod-tube" method by placement of rod made of Zr3/XV glass in tube made of SK222 glass and subsequently by thinning of preform to the 0.7 mm diameter.

Pulling of SK222 rods.

Preparation of preform

Preform structure for probe pulling consisted of two glass-metal rods of 0.7 mm diameter, optical fibre rod placed between them of 0.7 mm in diameter and SK222 glass rods. Whole set was placed in tube made of SK222 glass.

Probes thinning (pulling).

From prepared preform rods were pulled with internal 0.3-0.5 mm diameter with anaerobic atmosphere inside preform. As a result of the above process microprobe was prepared, which is illustrated on FIG. 3, 350 μm in diameter and containing metal electrodes A with 20 μm in diameter. Optical channel C for transmission of optical image is not placed exactly between electrodes, and its translocation happened in the step of preform thinning and is irrelevant for functionality of microprobe manufactured in this manner. Few metal electrode Only few discontinuities of metal electrodes were found in pulled probes. During selection over a dozen of probes 10 to 30 cm long containing continuous metal rods were chosen and selected for further application studies. Parameters of manufactured microprobes are enlisted below in Table 3.

TABLE 3

Geometric parameters of GM1A probes.

| Geometric parameters of GM1A probes | GM1A/2 | GM1A/3 |
| --- | --- | --- |
| Diameter of glass rod E [μm] | 458 | 352 |
| Diameters of metal electrodes A [μm] | 29 and 28 | 21 and 20 |
| Distance between metal electrodes A - [μm] | 37 | 31 |
| Diameter of optical channel [μm] | 28 | 23 |

Manufactured microprobes were connected to the external power supply by mounting of microprobes to the plates including mounting of metal electrodes A to the standard electric wires. Mounting of microprobe to the underlay plate was performed using microscope and micromanipulators. Epoxy glue was used. In the next step microelectrodes were connected with microscopic electric wires using Epo-Tek conductive adhesive. Microprobe was heated in oven in 300° C. temp. for 15 min. In these conditions glue was hardened. Bonding of A metal electrodes with macroscopic electric wires is depicted on FIG. 8. Rigid microprobe endings were obtained in this way enabling connection to electricity and to microprobe manipulation during experiment. Manufacturing of microprobe electrical connections shown on FIG. 7 enabled resistance measurement for metal electrodes A and measurement of breakdown voltage listed below in Table 4. Measurement was carried out under microscope because of need for metal electrode A length measurement and need for precise power connection.

TABLE 4

Summary of results for electrode resistance measurements in GM1A microprobe.

| Resistance [Ω] | A metal electrode length (from connector to connector) $(10^{-3})$[mm] |
| --- | --- |
| 33.8 | 117.98 |
| 34 | 118.48 |
| 70.8 | 154.72 |
| 41.4 | 154.87 |
| 31.6 | 98.13 |
| 28.3 | 96.27 |
| 86.5 | 97.03 |
| 70 | 94.99 |

Obtained results show low resistance of metal electrodes A what enables generation difference of potentials between two metal electrodes A without existence of unfavourable heat conditions in microprobe. It is also possible to utilize short electric pulses used in a few electroporation techniques.

Obtained results indicate that microprobe has electrodes with homogeneous diameter inside E glass rod. Subsequently, experiments were conducted leading to define breakdown voltage. Tests were conducted in aqueous solution of sodium chloride from zero concentration to obtaining of saturated solution in room temperature (26.5% concentration). Laboratory power adapter with regulated voltage in 0-30 V range was utilized to measure breakdown voltage. Performed tests have given negative results what means that breakdown voltage was higher than 30 V. That enables unconstrained usage of microprobe in aqueous environment (typical for laboratory cell cultures) without worries about breakdown and destruction of samples or microprobe.

Example 3—Electroporation Using Manufactured Microprobe According to the Invention Microprobes with 10-30 cm length and 350 μm in diameter with two metal electrodes A with about 20 μm in diameter, illustrated on FIG. 1, were manufactured. Metal electrodes A were exposed using etching with a solution of hydrofluoric acid, wherein acid to water ration in hydrofluoric acid was 1:1, and etching process lasted for 30 minutes. Resistance for measured microprobes 20-25 cm in length was equal to 30-80Ω. Tests performed in salt solution shown that breakdown voltage was higher than 30 V. Electroporation tests using manufactured microprobes were performed for opening of cell membrane and delivery of substances into the cells. 3-5 V voltage was applied to the microprobes. Two cell lines were used for studies: CHO-K1 cells—(ATCC® CCL-61™)—results of the studies were presented on FIG. 9a-c and H9C2 rat cardiac muscle cells were used. To verify the occurrence of cell electroporation phenomenon marker method using Trypan Blue was utilized. In cases of both cell lines it was unequivocally confirmed that electroporation is occurring in single cells in active range of microprobe. Migration of substances from the solution to the cell interior is an indication of occurrence of electroporation. It is possible to observe due to accumulation of marker in the cell which stains it blue. On FIG. 6a-c measurement results of CHO-K1 (ATCC® CCL-61™) cells electroporation were presented. During the experiment the distance between metal electrode A was equal to 226.93 µm, between its internal edges, and 277.83 µm between its external walls, electrode thickness was equal to 28.62 µm, and voltage and current intensity were respectively equal to: 1.7-2 V, 1.9 µA. Cells after electroporation (higher electrode) were stained with trypan blue and exhibited flattened morphology, what is illustrated on FIG. 9b. Cells placed in 300 micron distance from electrodes during the experiment (FIG. 9c) have not been electroporated and were left intact (so called control cells). Results of the electroporation experiment for rat cardiac muscle cell line—H9C2 were depicted on FIG. 10a-d. During the experiment distance between metal electrode A was equal to 156.46 µm, between its internal edges, and 207.83 µm between its external walls, metal electrode A thickness was equal to 27.11 µm, and voltage and current intensity were respectively equal to: 1.7-2 V, 1.9 µA. FIG. 10c shows a cell after electroporation near upper electrode in which a stained nucleus is visible. Cells which did not undergo electroporation (so called control cells) show no sings of staining according to the FIG. 10d.

The invention claimed is:

1. Microprobe for selective electroporation comprising:
a glass rod (E); and
at least two metal electrodes (A) immersed in the glass rod (E), wherein
the glass rod (E) is made of a primary glass, and the glass rod (E) has a diameter ranging from 50 µm to 2 mm,
the metal electrodes (A) are made of a metal alloy, the metal electrodes (A) are formed as rods, the metal electrodes (A) have a diameter ranging from 1 µm to 100 µm, and ends of the rods of the metal electrodes (A) are exposed, and
wherein the primary glass and the metal alloy are matched in such manner that a dilatometric softening temperature DTM of the primary glass is highly similar to a melting temperature of the metal alloy.

2. The microprobe according to claim 1, wherein the melting temperature of the metal alloy is lower than the dilatometric softening temperature DTM of the primary glass.

3. The microprobe according to claim 1, wherein the metal alloy is a silver alloy.

4. The microprobe according to claim 1, further comprises at least one air channel (B) for drug delivery, wherein the at least one air channel (B) is inside the glass rod (E).

5. The microprobe according to claim 1, further comprises at least one optical channel (C),
wherein the least one optical channel (C) is inside the glass rod (E), is made of a secondary glass, and is configured to transmit an optical signal.

6. The microprobe according to claim 1, further comprises at least one imaging channel (D),
wherein the at least one imaging channel (D) is inside the glass rod (E), is made of secondary glass, and is configured to transmit an optical signal.

7. The microprobe according to claim 6, wherein a refractive index nD of the primary glass is lower than a refractive index nD of the secondary glass.

8. The microprobe according to claim 6, wherein a linear thermal expansion coefficient of the primary glass and a linear thermal expansion coefficient of the secondary glass are similar.

* * * * *